(12) United States Patent
Herndon, Jr. et al.

(10) Patent No.: US 6,825,390 B1
(45) Date of Patent: Nov. 30, 2004

(54) STABILIZATION AND USE OF PROPARGYL BROMIDE

(75) Inventors: Robert C. Herndon, Jr., Baton Rouge, LA (US); Robert H. Allen, Baton Rouge, LA (US); Noel H. Brantley, Baton Rouge, LA (US); Hassan Y. Elnagar, Baton Rouge, LA (US); Ronny W. Lin, Baton Rouge, LA (US); Ralph W. Magin, Baton Rouge, LA (US); Mahmood Sabahi, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 177 days.

(21) Appl. No.: 10/126,260

(22) Filed: Apr. 18, 2002

(51) Int. Cl.$^7$ .................. C07C 17/00; C07C 17/02; C07C 17/04; C07C 17/08; C07C 21/00; C07C 23/00

(52) U.S. Cl. ................................ 570/217; 570/216
(58) Field of Search ..................... 570/217, 216

(56) References Cited

U.S. PATENT DOCUMENTS

| | | |
|---|---|---|
| 2,794,727 A | 6/1957 | Barrons |
| 3,009,853 A | 11/1961 | Youngson et al. |
| 3,541,168 A | 11/1970 | Pawloski et al. |
| 3,966,780 A | 6/1976 | Chodnekar et al. |
| 3,983,247 A | 9/1976 | Chodnekar et al. |
| 4,226,800 A | 10/1980 | Picklesimer |
| 4,833,157 A | 5/1989 | Kluender et al. |
| 5,063,771 A | 11/1991 | Vacquer |
| 5,405,989 A | 4/1995 | Shuto et al. |
| 5,508,295 A | 4/1996 | Hanson et al. |
| 5,874,576 A | 2/1999 | Huber |
| 6,319,611 B1 | 11/2001 | Mathias et al. |

FOREIGN PATENT DOCUMENTS

| | | |
|---|---|---|
| GB | 756674 | 9/1956 |
| GB | 925147 | 5/1963 |
| GB | 942348 | 11/1963 |
| GB | 1132417 | 10/1968 |

OTHER PUBLICATIONS

Author Unknown; "Toxic & Hazardous Industrial Chemical Manual For Handling and Disposal"; International Technical Information Inst.; Date Unknown; p. 441.
Barrons, Keith C.; "Methyl Bromide Alternative: Propargyl Bromide"; Farm Chemicals International; Nov. 2000; pp. 35–36.
Brandsma, L. et al.; "Improved Procedures For Bromopropadiene and Iodopropadiene"; Synthetic Communications, vol. 21; No. 1; 1991; pp. 69–72.
Coffee, Robert D. et al.; "Explosibility and Stabilization of Propargyl Bromide"; Eastman Kodak Co.; Loss Prevention., Symp. Houston, Texas; 1967; pp. 6–9.
Dowd, Paul et al.; "Preparation of Hexa–1, 5–Diyne–3–One"; Synthetic Communications, vol. 8; No. 4; 1978 pp. 205–209.
Forshey, D.R. et al.; "Potential Hazards of Propargyl Halides and Allene"; Bureau of Mines, USA; Fire Technology, 1969; vol. 5, Issue 2; pp. 100–111.
Henbest, H.B. et al.; "Researches on Acetylenic Compounds. Part XXI. Reformatsky Reactions With Propargyl Bromides"; Journal of the Chemical Society, 1949; pp. 2696–2700.
Henry, Louis; "On the Propargyl Compounds (Provisional Report)"; Chem. Ber.; vol. 6; 1873; pp. 728–730 (translation 4pages); Non–Translation (4 pages).
Wang, D. et al.; "Atmospheric Volatilization of Methyl Bromide, 1,3–dicloropropene, and Propargyl Bromide Through Two Plastic Films: Transfer Coefficient and Temperature Effect"; Atmospheric Environment; vol. 33; 1999; pp. 401–407.
Kern, R.D. et al.; "Thermal Decomposition of Propargyl Bromide And The Subsequent Formation of Benzene"; Combustion and Flame; 1995; pp. 177–184.
Konig, Burkhard et al.; "Triphenylphosphine–catalyzed Isomerisation of Propargyl Bromide to 1–Bromopropadiene"; Synthetic Communications; vol. 27; No. 10; 1997; pp. 1685–1688.
Kurginyan, K.A. et al.; "Synthesis of Bromoallene Under Conditions of Phase–Transfer Catalysis"; Plenum Publishing Corporation; 1986; pp. 2127–2130. (Translated from Zhurnal Organicheskoi Khimii, vol. 21; No. 11; Nov. 1985; pp. 2328–233).
Wu, Yuh–Wern et al.; "Photorearrangement of Propargyl Bromide as a Probe to Study Propargylic and Allenic Radicals by Infrared Matrix Isolation Technique"; Journal of The Chinese Chemical Society, 1998; vol. 45; pp. 307–312.
Yates, S.R. et al.; "Volatility, Adsorption, and Degradation of Propargyl Bromide as a Soil Fumigant"; J. Agric. Food Chemistry; 1998; vol. 46; pp. 755–761.

*Primary Examiner*—Samuel Barts
*Assistant Examiner*—Elvis O. Price
(74) *Attorney, Agent, or Firm*—Edgar E. Spielman, Jr.

(57) ABSTRACT

Propargyl bromide is effectively stabilized against shock or thermal decomposition by use therewith of an environmentally acceptable inert liquid solvent that forms an azeotrope with propargyl bromide.

31 Claims, No Drawings

STABILIZATION AND USE OF PROPARGYL BROMIDE

BACKGROUND

Propargyl bromide (3-bromopropyne) is known to be useful as a soil fumigant for control of fungi, nematodes, and undesirable plant life. See for example U.S. Pat. No. 2,794,727. For such usage it would be necessary to store and transport propargyl bromide from its manufacturing site to other locations and ultimately to farmlands where it would be put to use. And, in order to utilize propargyl bromide most effectively as a soil fumigant it would be desirable to have the ability to use it in pressurized dispensing systems wherein the pressurized fumigant is injected subsurface to the soil during cultivation.

Propargyl bromide is, however, a high energy material that is sensitive to physical shock or impact, and that is also susceptible to rapid thermal decomposition upon exposure to high temperatures or fires. In order to more safely produce, purify, store, transport, handle and use propargyl bromide, it is desired to stabilize the propargyl bromide against physical shock and exposure to elevated temperatures both in the liquid and vapor phase especially when in a confined space. In addition, since use of propargyl bromide as a soil fumigant would often involve having the product housed in pressurized systems or containers so that it can be injected into the soil, stabilization of propargyl bromide against physical shock and exposure to elevated temperatures when confined under pressure is another goal to be accomplished.

The hazardous character of propargyl bromide has been recognized heretofore, and certain stabilizing materials have been proposed for use. For example, as indicated in Brit. 1,132,417, propargyl bromide is shock sensitive, and when in a confined space, propargyl bromide may ignite spontaneously and decompose with explosive violence, and may detonate. To provide stabilization, Brit. 1,132,417 indicates that certain solvents were effective, namely toluene, xylene, a non-cyclic ether, tetrahydrofuran, dioxane, beta-ionone, and ethanol. Brit. 1,132,417 further points out that many organic liquids had been tried for the purpose of stabilizing propargyl bromide, but only a few had been successful, that no firm rule had been established for predetermining which liquids would be successful and which would not, and that among materials that were tested and found ineffective were hexane, benzene, chloroform, formamide, and light petroleum oil.

In a paper entitled "Explosibility and Stabilization of Propargyl Bromide", *Loss Prevention,* 1967, 1, 6–9, it is noted that propargyl bromide is sensitive to both shock and to temperature, and that under suitable conditions may be detonated, and that stabilization by dilution was explored as a possible solution to this problem. The authors of this paper report that at a diluent level of 15%, benzene, formamide, chloroform and hexane were judged by impact tests to be poor stabilizers for propargyl bromide, and that diethyl ether and diisopropyl ether appeared promising but were considered less attractive than toluene, xylene, and ethylhexylsorbitol. Based on processing considerations and impact test results, toluene and xylene were selected by the authors of this paper for further testing. In confinement tests toluene was judged by them to be the material of choice, especially at a dilution level of 20–30%. At present, propargyl bromide diluted with 20% of toluene is available as an article of commerce.

Unfortunately, toluene and xylene are both incapable of effectively stabilizing propargyl bromide in the vapor state. Thus conditions could be encountered in which propargyl bromide in admixture with toluene might nonetheless undergo explosive decomposition. Also, in order to use propargyl bromide as a soil fumigant it is important to avoid contaminating the soil with materials that leave residues that are not readily broken down by naturally-occurring microorganisms in the soil. Aromatic hydrocarbons such as toluene and xylene are not environmentally friendly as they are not rapidly consumed by such naturally-occurring microorganisms.

Thus a need exists for anew, environmentally-friendly way of effectively stabilizing propargyl bromide against both shock-induced and rapid heat-induced decomposition when in the vapor state and in the liquid state, and especially when under confinement under pressure. Because of the hazardous characteristics of propargyl bromide this need exists at all stages of its existence, including production, recovery, purification, handling, storage, transportation, and use.

Another need is for a more effective, environmentally-friendly, and less hazardous way of effecting space fumigation of enclosed spaces such as industrial and residential buildings, and especially of bulk commodities infested with or susceptible to infestation by pests, while being stored or transported in such closed spaces as bulk containers, bulk storage or transportation vessels or bins, silos, grain elevators, shipholds, bulk transport railway or road trucks, warehouses, storage sheds, and the like.

This invention enables fulfillment of these and other needs as well.

BRIEF SUMMARY OF THE INVENTION

It has been found that propargyl bromide can be effectively stabilized by combining propargyl bromide with an environmentally-acceptable inert liquid solvent that forms an azeotrope with propargyl bromide, such as a paraffinic and/or cycloparaffinic hydrocarbon solvent that forms an azeotrope with propargyl bromide. By "azeotrope" is meant a mixture that under temperature and pressure conditions encountered at any normal stage of the life-cycle of propargyl bromide, the propargyl bromide and a stabilizing amount of the hydrocarbon when in the liquid or vapor state remain together at all times. Thus the stabilization activity provided by the solvents used pursuant to this invention protects the propargyl bromide against hazardous shock-induced or thermally-induced decompositions whether the propargyl bromide is in the liquid state or in the vapor state. And accordingly, it is now possible to produce, recover, purify, handle, store, transport, and use propargyl bromide without fear of disastrous consequences, such as those resulting from rapid exothermic decomposition.

By "environmentally-acceptable" is meant that the inert liquid satisfies or, if not yet evaluated, will satisfy the requirements for listing as an "inert" or "other ingredients" in categorized List 1, List 2, List 3, or List 4 of the Office of Pesticide Programs of the United States Environmental Protection Agency, such lists as updated Jun. 12, 2001. Such lists are incorporated herein by reference as if fully set forth herein, except that all substances on such lists which do not meet all criteria specified herein are excluded from such lists because they are incapable or unsuitable for use in the practice of this invention.

Another embodiment of this invention is a closed container such as a drum, tank, tank car, tank trailer, or the like containing (i) a solution comprising propargyl bromide and a solvent that is compatible with propargyl bromide, and (ii)

a headspace or vapor space within said container, wherein said headspace or vapor space contains an inert gas such that the headspace or vapor space is devoid or substantially devoid of air and elemental oxygen. The solvent in this embodiment of the invention can be any solvent such as those described in Brit. 1,132,417, in the above paper entitled "Explosibility and Stabilization of Propargyl Bromide", *Loss Prevention*, 1967, 1, 6–9, or U.S. Pat. No. 2,794,727, such as toluene or zylene, but preferably is an environmentally-acceptable inert liquid solvent that forms an azeotrope with propargyl bromide. More preferably, the solvent results in the composition being classifiable as a "flammable liquid", in accordance with *Recommendations on the Transport of Dangerous Goods, Manual of Tests and Criteria,* 3rd Revised Edition, published by United Nations, New York and Geneva, 1999 (ISBN 92-1-139068-0).

Another aspect of this invention is the utilization of a vaporized propargyl bromide azeotropic composition of this invention in space fumigation.

The various embodiments of this invention will be still further apparent from the ensuing description and appended claims.

FURTHER DETAILED DESCRIPTION OF THE INVENTION

This invention enables propargyl bromide to be protected from the moment of its creation until the moment of its ultimate consumption, provided the material does not encounter some extraordinary set of conditions along the way. And even if the propargyl bromide encounters a dangerous condition such as a fire during storage or transportation, a collision during transportation, or excessive heat and pressure buildup during confinement, the severity and force of the decomposition of the propargyl bromide is greatly reduced.

Preferred compositions comprise a mixture of propargyl bromide, an inert liquid azeotropic solvent, and (i) a free radical inhibitor such as a sterically-hindered phenolic compound. Such compositions have been found to possess the additional advantage of resisting chemical transformation, e.g., chemical rearrangement to bromoallene, which can slowly occur during long periods of storage at ambient temperatures. As used herein "azeotropic" means that the solvent dissolves in propargyl bromide and forms an azeotrope with propargyl bromide so that a stabilizing amount of the solvent remains associated with the propargyl bromide at all times in both in the liquid state and in the vapor state.

Another group of preferred compositions comprise a mixture of propargyl bromide, an inert liquid azeotropic solvent, and an acid scavenger, such as epoxidized soybean oil. These compositions retain the excellent stability characteristics provided by the azeotropic solvent, and additionally are resistant to formation of color bodies and acid contaminants in the product.

Also preferred are compositions which comprise a mixture of propargyl bromide, an inert liquid azeotropic solvent, a free radical inhibitor such as a sterically-hindered phenolic compound, and an acid scavenger, such as epoxidized soybean oil. These compositions retain the excellent stability characteristics provided by the azeotropic solvent, resist chemical transformation, e.g., chemical rearrangement to bromoallene, and resist formation of color bodies and acid contaminants in the product.

Pursuant to preferred embodiments of this invention, there is provided a process of preparing propargyl bromide, which process comprises reacting in a reaction zone phosphorus tribromide and propargyl alcohol in an inert liquid azeotropic solvent that forms an azeotrope with propargyl bromide, to form a reaction mass containing propargyl bromide and said azeotropic solvent, and separating a mixture consisting essentially of propargyl bromide and said azeotropic solvent from the reaction mass, whereby a stabilizing amount of said azeotropic solvent is present with the propargyl bromide both in the liquid state and in the vapor phase (i) during the time the propargyl bromide is being formed and (ii) during and after the time propargyl bromide is being separated from the reaction mass. Preferably, the separated mixture of propargyl bromide and said azeotropic solvent is subjected to purification and optionally but preferably, to subsequent formulation with at least one other additive component, whereby propargyl bromide and a stabilizing amount of said azeotropic solvent remain together both in the liquid state and in the vapor phase at all times during the purification and the subsequent formulation operations. The resultant composition, whether or not subjected to the subsequent formulation, can then be packaged, stored, transported and used, whereby propargyl bromide and a stabilizing amount of said azeotropic solvent remain together both in the liquid state and in the vapor phase at all times during any and all such packaging, storage, transport and/or use. Preferably, a formulation step is carried out using (i) a free radical inhibitor such as a sterically-hindered phenolic compound, or (ii) an acid scavenger, such as epoxidized soybean oil, or both of (i) and (ii).

The term "inert" as used herein means that the solvent does not chemically react with the reactants used in producing the propargyl bromide under the conditions used for producing the propargyl bromide, and does not react with the propargyl bromide during the conditions used for producing the propargyl bromide or during normal conditions encountered during the recovery, purification, handling, storage, transportation, or use of the propargyl bromide.

By the term "stabilizing amount" with reference to the inert azeotropic solvent is meant an amount of the inert azeotropic solvent that is at least sufficient to provide a propargyl bromide composition that, if and when subjected in liquid form to the Bundesanstalt fur Materialprufung (BAM) Impact Test procedure as described in Example 5 hereinafter, exhibits no decomposition in any of 10 replicate tests. Although some azeotropic solvents are effective at even lower amounts, typically the minimum stabilizing amount of the azeotropic solvent combined with the propargyl bromide will be at least about 10 wt % of the composition. Preferably, the amount used should be at least about 15 wt % and more preferably at least about 20 wt % to provide a greater margin of safety. As a practical matter, the stabilized propargyl bromide product in the liquid state will normally not contain more than about 50 wt %, and preferably not more than about 35 wt %, of the azeotropic solvent. Preferably, the composition when in the vapor state exists at atmospheric pressure as a composition containing at least about 10 wt %, preferably at least about 15 wt %, and more preferably at least about 20 wt % of the solvent.

Still another embodiment of this invention is a method of controlling at least one pest selected from nematodes, fungi, and undesired plantlike, which method comprises applying to said at least one pest or to the locus thereof, or to both said at least one pest and the locus thereof, a mixture comprised of propargyl bromide and an inert liquid azeotropic solvent. Such mixture optionally but preferably is further comprised of (i) a free radical inhibitor such as a sterically-hindered phenolic compound, or (ii) an acid scavenger, such as epoxidized soybean oil, or both of (i) and (ii). In conducting this embodiment of the invention, different modes of operation are available for use. One such mode is to spray the pests and/or the locus of the pests with a biocidally-effective amount of an environmentally-friendly composition of this invention such as described above, typically in more diluted form. Another method comprises injecting a biocidally-effective amount of an environmentally-friendly composition of this invention into the soil, typically under increased pressure, such that the pests and their habitat in the soil are contacted by the composition.

Other type of pests which can be effectively controlled in an environmentally-friendly manner by the practice of this invention are pests which infest enclosed spaces within man-made structures. For example, industrial and residential buildings are typically infested, especially within enclosed wall, ceiling, and/or floor spaces, with various insect pests. Pursuant to this invention a biocidally-effective amount of an environmentally-friendly azeotropic composition of this invention is injected, typically under increased pressure as a vapor, fog, or fine mist into such enclosed spaces to effectively combat or control the infestation of pests. In preferred embodiments of this invention environmentally-friendly methods are provided for effecting space fumigation of enclosed spaces of bulk commodities infested with or susceptible to infestation by pests, while being stored or transported in such closed spaces as bulk containers, bulk storage or transportation vessels or bins, silos, grain elevators, shipholds, bulk transport railway or road trucks, warehouses, storage sheds, and the like. Such methods comprise introducing into the enclosed space, preferably in the form of an azeotropic vapor or fog, a biocidally effective amount of a composition comprised of propargyl bromide and an environmentally-acceptable inert liquid solvent that forms an azeotrope with propargyl bromide, such as a paraffinic and/or cycloparaffinic hydrocarbon solvent that forms an azeotrope with propargyl bromide.

In preferred embodiments of this invention, the propargyl bromide composition meets the requirements for classification as a "flammable liquid". In this connection attention is invited to *Recommendations on the Transport of Dangerous Goods, Manual of Tests and Criteria*, 3rd Revised Edition, published by United Nations, New York and Geneva, 1999 (ISBN 92-1-139068-0).

Various azeotropic solvents can be used in the practice of this invention. Non-limiting examples include n-heptane, mixed heptane isomers, cyclohexane, methylcyclohexane, 2-methylhexane, 2,4-dimethylpentane, -octane, isooctane, 2-methylheptane, 2,2-dimethylhexane, isopropyl alcohol, and a mixture of cyclohexane and isopropyl alcohol. A preferred solvent mixture is composed of a mixture of $C_{7-9}$ hydrocarbons (e.g, Isopar E, ExxonMobil Chemical Corporation) in admixture with cyclohexane. A particularly preferred azeotropic solvent is a mixture composed primarily of $C_8$ isoparaffinic hydrocarbons such as Isopar C (ExxonMobil Chemical Corporation).

As noted above, it is preferred to include an epoxide, preferably an epoxidized oil such as epoxidized soybean oil as a component of the compositions of this invention. It is also particularly preferred to further include a small amount of a hindered phenol such as 4-methyl-2,6-ditertbutyl phenol. Especially preferred mixtures are composed of about 60–70 wt % (e.g., 67.5 wt %) of propargyl bromide, about 30–35 wt % (e.g., 31 wt %) of Isopar C, about 0.5–5 wt % (e.g., 1 wt %) of epoxidized soybean oil, and about 0.05–0.7 wt % (e.g., 0.5 wt %) of 4-methyl-2,6-ditertbutyl phenol.

An additional and preferred option for any of the compositions of this invention is the presence of an inert gas such as nitrogen, helium, or argon. This minimizes or excludes oxygen from the composition, and usually results in a further decrease of the shock sensitivity of the propargyl bromide composition. For example, it has been discovered that adiabatic decomposition resulting from severe impact of propargyl bromide when in a confined space can be avoided by filling the head space above the liquid with an inert gas. Nitrogen is a preferred inert gas. The inert gas can be introduced into the composition by various means, such as blanketing the composition with an inert gas during its production, separation, and blending operations, and keeping it in a closed container under an inert atmosphere during storage and transportation.

It is advantageous to include an antioxidant (which is typically a free radical scavenger) in the composition of propargyl bromide to minimize isomerization of the propargyl bromide. Antioxidants or free radical scavengers that can be used with propargyl bromide include phenolic antioxidants, arylphosphites, and amines. Suitable phenolic antioxidants are typically sterically hindered phenolic antioxidants. Such antioxidants include, but are not limited to, 2-tert-butylphenol, 2-tert-amylphenol, 2,6-diisopropylphenol, 4-methyl-2-tert-butylphenol, 2,4-di-tert-butylphenol, 2,4-di-tert-butyl-5-methylphenol, 2,4-di-tert-butyl-6-methylphenol, 2,6-di-tert-butyl-4-methylphenol (also called BHT), 3,4-dimethyl-6-tert-butylphenol, 3,6-di-tert-butyl-4-(2-methyl butyl)phenol, 2,4,6-tri-tert-butylphenol, 4-tert-butylcatechol, 3-tert-butylresorcinol, methylenebis(2,6-di-tert-butylphenol), 1,3,5-trimethyl-2,4,6-tris(3,5-di-tert-butyl-4-hydroxybenzyl)benzene, and 2,5-di-tert-butylhydroquinone. Examples of arylphosphites that can be used are triphenylphosphite, tritolylphosphite, di(phenyl)(tolyl)phosphite, di(tolyl)(phenyl)phosphite, tri(naphthyl)phosphite, and tri(xylyl)phosphite. Amines that can be used as free radical scavengers which can be used are typically sterically-hindered amines. Preferred free radical scavengers are sterically hindered phenolic antioxidants. Highly preferred phenolic antioxidants are those that are U.S. Food and Drug Administration (FDA) approved, particularly when the composition is to be used for soil fumigation. Preferred hindered phenolic antioxidants are 2,6-di-tert-butylphenol, methylenebis(2,6-di-tert-butylphenol), and 2,6-di-tert-butyl-4-methylphenol; most preferred is 2,6-di-tert-butyl-4-methylphenol. Two or more different free radical scavengers may be used in a composition of the invention.

Acid scavengers in the composition prevent further reaction of acid decomposition products of propargyl bromide. Suitable types of acid scavengers include epoxides and epoxidized olefinically unsaturated oils. Examples of epoxides that can be used include, but are not limited to, 1,2-epoxypropane, 1,2-epoxybutane, 2,3-epoxybutane, 1,2-epoxyhexane, 1,2-epoxycyclohexane, 1,2-epoxyheptane, 1,2-epoxyoctane, 1,2-epoxydecane, 1,2-epoxycyclododecane, and styrene oxide. Epoxidized olefinically unsaturated oils that can be used include epoxidized babassu oil, epoxidized palm oil, epoxidized olive oil, epoxidized peanut oil, epoxidized rapeseed oil, epoxidized corn oil, epoxidized sesame oil, epoxidized cottonseed oil, epoxidized sunflower oil, epoxidized safflower oil, epoxidized hemp oil, epoxidized linseed oil, epoxidized lard oil, epoxidized neat's foot oil, and the like. Epoxidized olefinically unsaturated oils are preferred acid scavengers. Preferred is epoxidized soybean oil. Two or more acid scavengers can be used in a composition of the invention.

In the process of preparing propargyl bromide pursuant to this invention, propargyl alcohol, phosphorus tribromide, a stabilizing agent A) or B), optionally with a previously known stabilizing agent, such as toluene, and an amine catalyst are components of the reaction mixture. A reaction zone is formed at any point at which propargyl alcohol and phosphorus tribromide are brought into contact. This can result in the components coming together out-side of a typical reactor or reaction vessel. The reaction zone usually may be any of a variety of reactors or mixers. The reaction components can initially be brought into contact with each other in a mixing device in proximity to, but apart from, a reactor or reaction vessel. Suitable mixing devices include a static mixer, a conduit (preferably a conduit in which there is turbulent flow), or a jet mixer that produces a high velocity effluent stream. In all such cases, the mixing device itself in which propargyl alcohol and phosphorus tribromide first come into contact with each other is part of the reaction zone. Preferably, the reactants are concurrently fed into a reaction zone composed of at least one reactor or mixer in which all of the components—whether fed individually or in any subcombination(s)—all come together for the first time and in which the reaction to form propargyl bromide is initiated and carried out.

After the process of preparing propargyl bromide has been completed, at least one antioxidant and/or at least one acid scavenger may be added to the mixture.

For the process of preparing propargyl bromide, stabilizing agent A) and stabilizing agent B) are as described above for the propargyl bromide compositions. Preferred saturated hydrocarbons and amounts are also as detailed above. Small amounts of toluene, one more xylene isomers, or a mixture of any of these, may be present in the stabilizing agent.

Preferred saturated hydrocarbons and amounts for stabilizing agents A) and B) are as detailed above for the compositions.

The amine catalyst used in the process is normally a trihydrocarbyl amine. Amines that can be used as catalysts in a process of this invention include triethylamine, tributylamine, triphenylamine, tricyclohexylamine, and the like. Preferred amines are trialkylamines having up to 4 carbon atoms per alkyl group.

The process is normally conducted at one or more temperatures in the range of about to 10 about 80° C. More preferably, the reaction is conducted in the range of about to 20 about 70° C.; most preferably, the temperature is in the range of about to 25 about 60° C. during the process of the invention.

It has been found possible to achieve still further advantages in connection with the manner in which the processes of the invention are carried out. More particularly, by cofeeding the reaction components, including the stabilizing agent, into the reactor or reaction zone, substantial additional advantages are obtained. The advantages of such cofeeding of the reaction components are that the temperature increase which happens during the reaction occurs more slowly, and that the temperature does not rise to as high a value as it does when phosphorus tribromide is added to a propargyl alcohol solution containing amine catalyst. This in turn is less demanding on cooling equipment. Typical high temperatures for a cofeed operation when adding phosphorus tribromide to a propargyl alcohol solution containing amine catalyst are about 40° C. to about 70° C.

When conducting a cofeed operation, the components should be fed so that the propargyl alcohol and the phosphorus tribromide contact each other in the presence of stabilizing agent. These components may be fed separately, or the agent may be fed in combination with the propargyl alcohol, the phosphorus tribromide, or in combination with both. Propargyl alcohol and phosphorus tribromide should not be fed together as the same feed. The amine catalyst may be co-fed singly, with agent, with propargyl alcohol, with phosphorus tribromide, or with any two or more of the other feeds. Cofeeding does not have an adverse effect on the yield of propargyl bromide (as compared to yields obtained when feeding phosphorus tribromide to a propargyl alcohol solution containing amine catalyst).

Each of the various feeds in the cofeed operation may be continuous or intermittent. Further, there is no requirement that any of the feeds occur simultaneously with any of the other feeds. For example, the separate feeds need not start or end at precisely the same time. Instead, there can be a suitably short time between the start of one feed and another, while still realizing the advantages of the cofeed operation. The point here is that the duration of the cofeeds should be sufficient to obtain the foregoing advantages, but need not be exactly coextensive in time.

For a cofeed operation, stabilizing agent A) and stabilizing agent B) are as described above for the process of preparing propargyl bromide. Preferred saturated hydrocarbons and amounts are also as detailed above. Small amounts of toluene, one more xylene isomers, one or more non-cyclic ethers, tetrahydrofuran, dioxane, beta-ionone, ethanol, or a mixture of any of these, may be present in the stabilizing agent. Although less preferred, toluene, one more xylene isomers, one or more non-cyclic ethers, tetrahydrofuran, dioxane, beta-ionone, ethanol, or a mixture of any of these may be used as the stabilizing agent for the cofeed operation.

When distilling propargyl bromide from the crude reaction product, use of a stabilizing agent having a boiling point similar to that of propargyl bromide is desirable because the stabilizing agent distills with the propargyl bromide. The presence of stabilizing agent in the vapor phase with propargyl bromide minimizes the shock sensitivity of propargyl bromide in the vapor phase. When a mixture of two or more saturated hydrocarbons is used, at least one of which has a boiling point lower than that of propargyl bromide and at least one of which has a boiling point higher than that of propargyl bromide, it is usually necessary to add more of the lower-boiling hydrocarbon(s) during distillation of propargyl bromide so that the lower-boiling hydrocarbon(s) does not become depleted from the mixture. Without being bound by theory, it is believed that saturated hydrocarbons form azeotropes with propargyl bromide, which causes such agent to always be present with the propargyl bromide whenever it vaporizes. The concentration of propargyl bromide would thus never increase above the azeotrope concentration, rendering the distillation inherently safe.

In the embodiments of this invention wherein pests are combatted or controlled by use of a composition of this invention, any biocidally-effective amount of the composition can be used. Such amount will of course vary depending upon the type of pests being controlled or killed, the location in which the pests are present, the amount and type of commodity within the enclosed space, and the type or mode of application being used. For example, where agricultural bulk or prepared commodities such as flour, beans, wheat, corn, soy beans, barley, peanuts, cocoa beans, coffee, rice, farinaceous products, fruit, vegetables, flowers, timber, and the like are present within an appropriate enclosed space such as a storage bin, silo, grain elevator, cargo vessel, aircraft, road vehicle, etc., the amount of propargyl bromide in vaporized form is preferably at least sufficient to thoroughly penetrate the contents of the enclosed space yet not leave an excessive residue on the commodities being treated.

A carrier gas, such as nitrogen, argon, or carbon dioxide, which may be heated if desired, can be used for delivering the propargyl bromide azeotropic composition through the commodity being treated. Alternatively the vaporized propargyl bromide azeotropic composition can be employed in a larger quantity tending to leave a larger amount of residue on the commodity, followed by a purging or aeration operation with air or an inert non-toxic gas such as nitrogen or carbon dioxide, so as to suitably reduce residual or virtually eliminate levels of the fumigant on the commodity. Suitable methods for estimating fumigant residues in commodities are known and can be used if desired. See for example U.S. Pat. No. 5,069,06 1. In general, the amounts of propargyl bromide on a molar basis are comparable to amounts of methyl bromide previously used in the same or an analogous space fumigation operation. A typical amount of active fumigant (i.e., propargyl bromide) introduced into the enclosed space is in the range of about 1 to about 10 pounds per thousand cubic feet of volume. Preferred amounts are in the range of about 2 to about 5 pounds per thousand cubic feet of volume. However departures from these ranges are permissible and within the scope of this invention, since conditions can vary substantially from case to case. In a preferred operation, after completion of the space fumigation step, the enclosed space is aerated with fresh air or non-toxic gas (preferably nitrogen or carbon dioxide) and even more preferably, the propargyl bromide is purged from the aeration gas by passing the stream through a suitable absorbent or other retentive substrate. Such operations are facilitated because of the azeotropic character of the azeotropic compositions of this invention even when in the vapor state. Procedures and apparatus similar to those used or proposed for purging methyl bromide from gaseous streams can be used for this purpose. Note for example, U.S. Pat Nos. 5,505,908 and 5,904,909. In the space fumigation processes of this invention fans or blowers can be used for propelling the vaporized azeotropic compositions into and through the encased commodity.

EXAMPLES

The following examples are illustrative and are not to be taken as limiting the invention.

Example 1

An 18" spinning band distillation column was employed. A vacuum system was attached to the distillation setup, allowing sub-atmospheric pressures to be achieved. Approximately 50 mL of material was required for each set of runs. Reflux and collection of distillate were controlled manually. A small amount (1–2 mL) of distillate was collected at a high reflux ratio. Analyses were performed using proton NMR spectroscopy, and the integrated peaks were normalized.

Seven sets of runs were performed. Each set of runs used a different solvent or solvent system. Set 1 was a calibration run, and was performed using a mixture of cyclohexane and isopropanol at atmospheric pressure. The results of Set 1 are shown in Table 1. Sets 2–7 were distillations of propargyl bromide and a solvent at different pressures. Table 2 presents the experimentally determined azeotrope compositions in the distillate for propargyl bromide with cyclohexane (Set 2), n-heptane (Set 3), heptanes (Set 4), isooctane (Set 5), Isopar C (Set 6), and methylcyclohexane (Set 7), respectively.

TABLE 1

| Set 1 | Cyclohexane | Isopropanol | Temp. |
|---|---|---|---|
| Starting material | 49.4 wt % | 50.6 wt % | |
| Distillate | 67.3 wt % | 32.7 wt % | 69.6° C. |
| Literature values* | 68 wt % | 32 wt % | 69.4° C. |
| for distillate | 67.3 wt % | 32.7 wt % | 69.6° C. |
| | 67 wt % | 33 wt % | 68.6° C. |
| | 67.0 wt % | 33.0 wt % | 68.8° C. |

*Literature values are from Horsley, Azeotrope III, New York.

TABLE 2

| | Propargyl bromide | Bromoallene | Propargyl alcohol | Solvent | Temp. |
|---|---|---|---|---|---|
| Set 2 | | | | Cyclohexane | |
| Starting material | 50.08 wt % | 0.32 wt % | | 49.60 wt % | n/a |
| 81 mmHg | 48.68 wt % | 0.56 wt % | | 50.77 wt % | 18.0° C. |
| 200 mmHg | 50.83 wt % | 0.60 wt % | | 48.57 wt % | 35.8° C. |
| 395 mmHg | 52.66 wt % | 0.52 wt % | | 46.82 wt % | 53.2° C. |
| 755 mmHg | 54.73 wt % | 0.50 wt % | | 44.77 wt % | 72.8° C. |
| Set 3 | | | | n-Heptane | |
| Starting material | 67.81 wt % | 0.43 wt % | | 31.77 wt % | n/a |
| 84 mmHg | 72.23 wt % | 2.01 wt % | | 25.77 wt % | 22.4° C. |
| 205 mmHg | 73.76 wt % | 2.06 wt % | | 24.18 wt % | 42.3° C. |
| 396 mmHg | 74.94 wt % | 1.21 wt % | | 23.84 wt % | 59.5° C. |
| 755 mmHg | 76.79 wt % | 0.94 wt % | | 22.26 wt % | 78.8° C. |
| Set 4 | | | | Heptanes[1] | |
| Starting material | 65.02 wt % | 0.46 wt % | | 34.52 wt % | n/a |
| 82 mmHg | 64.81 wt % | 1.25 wt % | | 33.94 wt % | 20.1° C. |
| 753 mmHg | 68.62 wt % | 1.76 wt % | | 29.62 wt % | 76.1° C. |

TABLE 2-continued

|  | Propargyl bromide | Bromoallene | Propargyl alcohol | Solvent | Temp. |
|---|---|---|---|---|---|
| Set 5 |  |  |  | Isooctane |  |
| Starting material | 70.26 wt % | 0.46 wt % |  | 29.28 wt % | n/a |
| 79 mmHg | 66.71 wt % | 1.82 wt % |  | 31.47 wt % | 20.3° C. |
| 754 mmHg | 73.03 wt % | 1.57 wt % |  | 25.40 wt % | 78.7° C. |
| Set 6 |  |  |  | Isopar C[2] |  |
| Starting material | 70.03 wt % | 0.47 wt % |  | 29.5 wt % | n/a |
| 81 mmHg | 66.7 wt % | 1.34 wt % |  | 32.0 wt % | 20.8° C. |
| 200 mmHg | 67.41 wt % | 2.42 wt % |  | 30.02 wt % | 40° C. |
| 300 mmHg | 69.50 wt % | 1.67 wt % |  | 28.21 wt % | 51° C. |
| 450 mmHg | 71.28 wt % | 1.27 wt % |  | 27.44 wt % | 62° C. |
| 761 mmHg | 72.96 wt % | 1.17 wt % |  | 25.87 wt % | 78.9° C. |
| Set 7 |  |  |  | Methylcyclohexane |  |
| Starting material | 67.31 wt % | 0.93 wt % | 0.23 wt % | 31.53 wt % | n/a |
| 81 mmHg | 66.45 wt % | 4.85 wt % | 1.31 wt % | 27.39 wt % | 22.2° C. |
| 753 mmHg | 71.97 wt % | 4.44 wt % | 2.46 wt % | 21.13 wt % | 79.6° C. |

[1]Heptanes (VWR Chemical Company) contain, as determined by gas chromatography/mass spectroscopy: 36.8 area % n-heptane, 27.2 area % 3-methylhexane, 19.2 area % 2-methylhexane, with the remainder being other $C_7$ isomers, with traces of $C_6$ and $C_8$ compounds.
[2]Isopar C (ExxonMobil Company) is a mixture, predominately of $C_8$ isomers, and is about 80% isooctane.

Example 2

Since propargyl bromide is both toxic and impact sensitive, the distillation apparatus was assembled so that it could be operated remotely, which minimized the hands-on interaction of an operator with the distillation unit. To ensure that the propargyl bromide could not be confined, which could have led to a violent deflagration or detonation, the apparatus was constructed of glass with Teflon (PFA & PTFE) connecting tubing. There was a one-foot space between the apparatus and the wall of the high pressure cell so that in the event of an explosion, all damage would be contained within the cell. In addition, to keep temperatures low, vacuum distillations were performed.

The kettle was a 5-liter jacketed round bottom flask. Heat was applied to the kettle via a heating bath (1:1 ethylene glycol/water mixture). The heating bath temperature was 70° C. for all of the distillations in this Example. The heating bath was placed around the wall of the high pressure cell which allowed its operation without direct exposure to the distillation assembly. A Teflon-coated magnetic stir bar was used to help mix the contents of the kettle. The temperature of the kettle was monitored via a stainless steel thermocouple, and pressure was monitored via a stainless steel transducer. A 2-inch inner diameter vacuum-jacketed column packed with 36 inches of 0.24-inch 316 stainless steel Pro-Pak packing was used for the distillations of propargyl bromide from crude reaction product. For distillations of propargyl bromide from toluene solution, a 100 liter flask, a glass column, and approximately 8 feet of 0.24-inch 316 stainless steel packing (Pro-Pak®, Ace Glass Incorporated, Vineland, N.J.) were used.

The distillate was a clear, water white liquid in all distillation runs. The material from Run 1 unknowingly contained cyclohexane and was discarded. During Run 3 (batch 5), a slop cut was taken (first 82 grams of 1019 grams total distillate). The slop cut contained 0.84 wt % bromoallene, whereas the second (main) cut contained 0.082 wt % bromoallene. This run showed that it is possible to separate bromoallene from propargyl bromide by distillation.

Runs 1–11 were distillations of crude reaction product mixture which contained approximately 42 wt % propargyl bromide. The typical procedure was to water wash the product crude at the conclusion of the reaction. The crude reaction product used in Run 9 (batch 12) was not water washed prior to distillation. The Run 9 (batch 12) material had solids present as a result, and had a very low concentration of propargyl alcohol. During all other runs distilled from crude reaction product, propargyl alcohol was a major impurity in the distillate. No propargyl alcohol was detected in the distillate from Run 9 (batch 12). This Run shows that propargyl bromide containing significantly less than 0.1 wt % propargyl alcohol can be produced by using non-water-washed reaction crude.

Runs 12–15 (Batches 3, 4, 10, and 15) started with a solution containing 80 wt % propargyl bromide and 20 wt % toluene (Honjo Chemical Company). Run 14 (Batch 10) was distilled after cyclohexane had been added to the mixture to be distilled. For safety reasons, it was desired to never have propargyl bromide at high concentrations (>approximately 95%). To accomplish this, cyclohexane was continuously fed to the kettle. The results of this run proved that this is a viable technique for diluting the vapor phase of propargyl bromide. All of the cyclohexane fed to the column ended up in the distillate. In Run 15 (Batch 15), Isopar C (mixture, predominately of $C_8$ isomers, about 80% isooctane; Exxon-Mobil Company) was charged to the system along with the propargyl bromide solution before the start of the distillation. Again, it was desired to never have propargyl bromide at high concentrations (>approximately 95%). Isopar C and propargyl bromide formed a minimum boiling azeotrope. rope composition of roughly 69 wt % propargyl bromide and 31 wt % Isopar C was in the distillate.

The distillations produced neat propargyl bromide (approximately 99 wt %) either solution of 80 wt% propargyl bromide plus 20 wt % toluene or from crude reaction mixture. Results are summarized in Table 3.

The formation of bromoallene in these solutions reached a maximum of about 4.5 to 5% and then its concentration decreased. The drop in concentration of 1-bromoallene and propargyl bromide is probably the result of the formation of oligomeric and/or polymeric material. A black solid could be seen at the bottom of the NMR tubes.

Other impurities were present in the solutions. The propargyl aldehyde level was 0.1 wt %, with the maximum

TABLE 3

| Run | | Batch | Propargyl bromide | Bromo-allene | Propargyl alcohol | 1,3-dibromo-propene | 2,3-dibromo-propene | Toluene | Other |
|---|---|---|---|---|---|---|---|---|---|
| 1 | start 3028.5 g | 1 | — | — | — | — | — | | |
|  | distillate | | 682.4 g | 5.9 g | 8.4 g | 0 | 0 | 0.4 g | 142.8 g cyclohexane |
| 2 | start 3115.4 g | 2 | 1283.5 g | 8.7 g | 7.8 g | 41.4 g | 112.2 g | 1660.5 g | |
|  | distillate | | 1124.2 g | 7.2 g | 6.9 g | 0 | 0 | 1.9 g | 2.1 g cyclohexane |
| 3 | start 2840.5 g | 5 | 1195.3 g | 1.7 g | 5.4 g | 25.0 g | 62.7 g | 1550.3 g | |
|  | distillate | | 1011.3 g | 1.46 g | 4.91 g | 0 | 0 | 0.67 g | 0.88 g HCs[1] |
| 4 | start 2975.1 g | 6 | 1273.3 g | 0 | 0 | 31.2 g | 69.9 g | 1598.2 g | |
|  | distillate | | 860.6 g | 63 g | 4.0 g | 0 | 0 | 0.6 g | 0.6 g HCs[1], 0.4 g $H_2O$ |
| 5 | start 2627.2 g | 7 | 1124.4 g | 0 | 0 | 27.6 g | 61.7 g | 1411.3 g | |
|  | distillate | | 986.9 g | 2.64 g | 5.7 g | 0 | 0 | 1.8 g | 0.54 g HCs[1], 0.37 g $H_2O$ |
| 6 | start 3208 g | 8 | 1373.0 g | 0 | 0 | 33.7 g | 75.4 g | 1723.3 g | |
|  | distillate | | 1200.8 g | 8.8 g | 5.9 g | 0 | 0 | 1.33 g | 0.77 g HCs[1], 0.62 g $H_2O$ |
| 7 | start 3297.6 g | 9 | 1385.0 g | 16.2 g | 6.3 g | 36.3 g | 93.3 g | 1754.3 g | 1.1 g HCs[1], 3.6 g $H_2O$ |
|  | distillate | | 1223.5 g | 14.7 g | 6.2 g | 0 | 0 | 1.2 g | 0.7 g HCs[1], 0.3 g $H_2O$ |
| 8 | start 2250 g | 11 | 1002.6 g | 2.3 g | 4.5 g | 25.0 g | 61.9 g | 1152 g | 0.2 g HCs[1], 1.6 g $H_2O$ |
|  | distillate | | 872.0 g | 2.1 g | 4.0 g | 0 | 0 | 1.3 g | 0.4 g HCs[1], 0.2 g $H_2O$ |
| 9 | start 2241 g | 12 | 1042.3 g | 3.3 g | 0.4 g | 26.7 g | 85.7 g | 1080.4 g | 0.4 g HCs[1], 1.9 g acetone |
|  | distillate | | 907.2 g | 2.5 g | 0 | 0 | 0 | 1.4 g | 0.1 g HCs[1], 1.4 g acetone, 0.3 g $H_2O$ |
| 10 | start 2276.5 g | 13 | 1012.9 g | 11.6 g | 3.0 g | 25.8 g | 62.9 g | 1157.1 g | 0.5 g HCs[1], 2.7 g $H_2O$ |
|  | distillate | | 795.1 g | 9.4 g | 2.3 g | 0 | 0 | 0.5 g | 0.2 g HCs[1] |
| 11 | start 2650 g | 14 | 1145.9 g | 8.0 g | 5.4 g | 27.5 g | 66.4 g | 1395.9 g | 0.8 g HCs[1] |
|  | distillate | | 920.0 g | 6.9 g | 4.5 g | 0 | 0 | 1.9 g | 6.6 g HCs[1] |
| 12 | start 2939.6 g | 3 | 2334.0 g | 13.2 g | 0.6 g | 0 | 13.2 g | 578.2 g | |
|  | distillate | | 1972.3 g | 6.5 g | trace | 0 | 0 | 0 | 0.4 g THF, 0.6 g cyclohexane |
| 13 | start 3267 g | 4 | 2594.0 g | 14.7 g | 0.7 g | 0 | 14.7 g | 643.6 g | |
|  | distillate | | 2293.2 g | 7.1 g | 0 | 0 | 0 | 0 | 0.5 g THF, 0.9 g cyclohexane |
| 14 | start 1900 g | 10 | 1501.7 g | 10.7 g | 0.27 g | 0 | 8.1 g | 379 g | 0.2 g HCs[1] |
|  | distillate | | 1496.3 g | 11.8 g | 0 | 0 | 0 | 0.2 g | |
| 15 | start 2388 g | 15 | 1330.5 g | 10.3 g | 0.2 g | 0 | 7.6 g | 335.7 g | 703.7 g Isopar C[2] |
|  | distillate | | 1017.0 g | 8.0 g | 7.2 g | 0 | 0 | 0 | 460.7 g Isopar C[2] |

[1]HCs is an abbreviation for hydrocarbons.
[2]Isopar C (ExxonMobil Company) is a mixture, predominately of $C_8$ isomers, and is about 80% isooctane.

Example 3

Heavy walled 1.5 mL glass vials with Teflon-lined septum caps were used to oven age three-component propargyl bromide formulations. The septum caps were to provide a path of least resistance if a pressure build-up occurred. No such pressure build-up was ever observed, but some of the vials leaked. In these runs, temperatures of about 50° C. were used.

Very similar decomposition rates were seen at 110° C. for the toluene, Soygold 1000, and Exxsol D80 solutions. The results in DF9 were slightly different from the other solutions.

concentration occurring at the beginning and decreasing with time. Other aldehydes were initially less than 0.4%, and decreased with time. Dibromopropenes were present as three isomers at 1–3% after 135 hours. Propargyl alcohol and propargyl chloride were both present at less than 0.1 %.

The only significant reaction occurring at 50° C. over time is the isomerization of propargyl bromide to bromoallene. After 84 days, the bromoallene level increased from 0.26% to 0.57%.

TABLE 4

| Initial sample composition | | | | | | |
|---|---|---|---|---|---|---|
| Propargyl bromide | Other components | Container | Temp. | Time elapsed | Propargyl bromide | Bromoallene |
| 72.4 wt % | 18.1 wt % Toluene, 9.5 wt % toluene-d8, 0.71 wt % bromoallene | NMR tube | 110° C. | 15 hr. 33 hr. 50 hr. 117 hr. 135 hr. | 71 wt % 64 wt % 57.9 wt % 38.3 wt % 34.1 wt % | 2.3 wt % 3.4 wt % 4.0 wt % 3.7 wt % 3.9 wt % |
| 72.4 wt % | 18.1 wt % Toluene, 9.5 wt % toluene-d8, sparged with N₂ | NMR tube | 110° C. | | | |
| 80 wt % | 20 wt % Soygold¹, sparged with N₂, 0.38 wt % bromoallene | NMR tube | 110° C. | 17 hr. 67 hr. 85 hr. 146 hr. 168 hr. | 73.5 wt % 51.2 wt % 43.1 wt % 26.8 wt % 21.1 wt % | 2.00 wt % 4.30 wt % 4.7 wt % 4.8 wt % 4.6 wt % |
| 80 wt % | 20 wt % DF#9², sparged with N₂, 0.76 wt % bromoallene | NMR tube | 110° C. | 17 hr. 67 hr. 85 hr. 146 hr. 168 hr. | 72.1 wt % 41.6 wt % 33.8 wt % 18.8 wt % 13.8 wt % | 3.2 wt % 4.5 wt % 4.3 wt % 3.4 wt % 2.8 wt % |
| 80 wt % | 20 wt % Exxsol D80³, sparged with N₂, 0.36 wt % bromoallene | NMR tube | 110° C. | 15 hr. 32 hr. 50 hr. 117 hr. 135 hr. 196 hr. | 71.4 wt % 63.9 wt % 57.0 wt % 35.8 wt % 29.4 wt % 15.5 wt % | 2.5 wt % 3.6 wt % 4.0 wt % 4.2 wt % 3.9 wt % 3.5 wt % |
| 81 wt % | 15 wt % DF#9², 4 wt % epoxidized soybean oil | glass vial | 50° C. | leaked; study stopped | | |
| 68 wt % | 25 wt % DF#9², 7 wt % epoxidized soybean oil | glass vial | 50° C. | leaked; study stopped | | |
| 75 wt % | 20 wt % Exxsol D80³, 5 wt % epoxidized soybean oil | glass vial | 50° C. | leaked; study stopped | | |
| 68 wt % | 25 wt % Soygold¹, 7 wt % epoxidized soybean oil, 0.2 wt % bromoallene | glass vial | 50° C. | 168 hr. ~450 ~750 ~1000 ~1340 ~2000 | 6_ wt % 6_ wt % 6_ wt % 6_ wt % 6_ wt % 6_ wt % | 0.2_ wt % 0.2_ wt % 0.3_ wt % 0.3_ wt % 0.5_ wt % 0.5_ wt % |

[1]Soygold 1000 is a methylated soybean oil product comprised of methylated soybean oil.
[2]DF#9 is a naphthalene depleted aromatic hydrocarbon fluid, obtained from ExxonMobil Chemical Corporation.
[3]Exxsol D80 consists mainly of non-aromatic hydrocarbons with an IBP of 200° C. minimum and a DP of 248° C. max. It is a product of ExxonMobil Chemical Corporation.

Example 4

A group of samples was prepared, varying the amount of water, 2,6-di-tert-butyl-4-methylphenol (BHT), and epoxidized soybean oil (ESO) added to each propargyl bromide solution. Mesitylene was added as an internal standard for NMR spectroscopy. Deuterated benzene was also added as an internal NMR standard. The starting compositions were made up of 80 wt % propargyl bromide, 10 wt % mesitylene, the varying amounts of water, BHT, and ESO, and enough $C_6D_6$ to make the components add up to be 100 wt %. The oven-aging experiments were conducted by sealing each sample in an NMR tube and placing each sample in an oven, either an oven set at 50° C. or in an oven set at 60° C. The concentration of the components in the test solutions are shown in Table 5; the concentrations of the additives for each Run are shown in Table 5. "Low" water refers to less than 0.1 wt %.

Under conditions of low water at a temperature of 50° C., the presence of 3% ESO seems to favor the formation of 1-bromoallene. Under conditions of low water and a temperature of 60° C., the presence of 3% ESO has a beneficial effect but high BHT shows the greatest beneficial effect, regardless of the level of ESO.

TABLE 5

| Starting composition (80 wt % propargyl bromide, 10 wt % mesitylene, and $C_6D_6$ to reach 100 wt %) | | | | |
|---|---|---|---|---|
| Run | H₂O | BMT[1] | ESO[2] | Temp. |
| 1 | low | 0.1 wt % | 1 wt % | 50° C. |
| 2 | low | 0.1 wt % | 3 wt % | 50° C. |
| 3 | low | 0.5 wt % | 1 wt % | 50° C. |
| 4 | low | 0.5 wt % | 3 wt % | 50° C. |
| 5 | 0.1 wt % | 0.1 wt % | 1 wt % | 50° C. |
| 6 | 0.1 wt % | 0.1 wt % | 3 wt % | 50° C. |
| 7 | 0.1 wt % | 0.5 wt % | 1 wt % | 50° C. |
| 8 | 0.1 wt % | 0.5 wt % | 3 wt % | 50° C. |
| 9 | low | 0.1 wt % | 1 wt % | 60° C. |
| 10 | low | 0.1 wt % | 3 wt % | 60° C. |
| 11 | low | 0.5 wt % | 1 wt % | 60° C. |
| 12 | low | 0.5 wt % | 3 wt % | 60° C. |
| 13 | 0.1 wt % | 0.1 wt % | 1 wt % | 60° C. |
| 14 | 0.1 wt % | 0.1 wt % | 3 wt % | 60° C. |

TABLE 5-continued

Starting composition
(80 wt % propargyl bromide, 10 wt %
mesitylene, and C₆D₆ to reach 100 wt %)

| Run | H₂O | BMT[1] | ESO[2] | Temp. |
|---|---|---|---|---|
| 15 | 0.1 wt % | 0.5 wt % | 1 wt % | 60° C. |
| 16 | 0.1 wt % | 0.5 wt % | 3 wt % | 60° C. |

[1]BHT is 2,6-di-tert-butyl-4-methylphenol.
[2]ESO is epoxidized soybean oil.

Example 5

The impact tester used in this Example was manufactured by Adolf Kuhner AG (Switzerland), and is a "Falling Hammer Test" model, MP-3. No concrete foundation was used to support the device. The lack of a concrete foundation does not affect the operation of the apparatus or the results. The impact tester has a steel cylindrical base, 280 mm in diameter and 280 mm in height. Attached to the base are two rods used to guide the 5 kg drop weight. The falling height is adjustable, with a maximum falling height of approximately 100 cm. The maximum available impact energy from this device is 49 J. The drop weight is equipped with a brake which automatically engages after initial impact with the sample, which prevents the weight from making multiple strikes on the sample assembly. The sample assembly, of the Bundesanstalt fur Materialprufung (BAM, Berlin) design, is recommended by the United Nations for testing explosives and explosive articles (*Recommendations on the transport of Dangerous Goods, Manual of Tests and Criteria*, 2nd revised edition), and can be used for both solids and liquids. This sample assembly consists of two stainless steel cylinders inserted into a guide ring and sitting on a guide block.

Impact sensitivity was determined by loading the BAM sample assembly with 40 microliters of sample, being careful not to encase air in the assembly, then allowing the drop weight to strike the sample assembly. In some of the runs an air bath was used to heat the entire kuhner drop weight tester. The air bath consisted of a wooden and Plexiglas enclosure containing two finned strip heaters controlled by a temperature controller. A small fan was used to circulate the air inside the enclosure. This air bath could control the temperature to within ±1° C. A temperature of 50° C. was used.

The BAM procedure calls for six trials to be run at given drop weight and height for each sample. The sample passes the test for the given conditions if no reaction occurs in any of the six trials. However, the standard chosen for a sample failing was that if at least one out of ten trials results in a reaction, the sample fails the test.

A reaction was typically accompanied by an audible "bang", smoke, fire, and/or sparks. However, some samples decomposed under impact without any of these indicators. In these instances, a reaction occurred if the residue in the sample assembly was that of decomposition products (black soot, char; significant discoloration). When neat propargyl decomposed in this device, smoke was observed along with an audible report; black char and soot were all that remained upon opening the test cell.

At least ten replicate experiments were performed for each entry in Tables 6–8. A "yes" indicates at least one decomposition occurred, and a "no" indicates no decomposition in any of the ten replicate experiments. Table 6 presents impact testing results for sample compositions dropped from more than one height. Table 7 presents results for sample compositions dropped only from a height of 100 cm. All of the data presented in Table 7 consists of runs in which the 5 kg weight was dropped from a height of 100 cm. Mixtures of propargyl bromide with saturated hydrocarbons, especially cyclohexane, were less prone to decomposition.

TABLE 6

| Sample composition | | Drop height | | | | | | | |
|---|---|---|---|---|---|---|---|---|---|
| Propargyl bromide | Other components | 10 cm | 20 cm | 30 cm | 40 cm | 60 cm | 80 cm | 90 cm | 100 cm |
| 0 wt % | 100 wt % Nitromethane | | | | no | | | | no |
| 100 wt % | none | yes | yes | yes | yes | | | yes | yes |
| 100 wt % | none | yes | yes | | | | | | |
| 80 wt % | 20 wt % Toluene | | | no | | | | | no |
| 80 wt % | 20 wt % A150ND[1] | | | no | | no | no | no | no |
| 80 wt % | 20 wt % Soygold 1000[2] | | | no | | | no | | no |
| 80 wt % | 20 wt % Isopar M[3] | | | no | | | no | | no |
| 80 wt % | 20 wt % Exxsol D80[4] | | | no | | | no | | no |
| 80 wt % | 13 wt % A150ND[1], 7 wt % ESO | | | no | | | no | | no |

[1]A150ND is a naphthalene depleted aromatic 150 hydrocarbon fluid.
[2]Soygold 1000 is a methylated soybean oil product comprised of methylated soybean oil
[3]Isopar M is a non-aromatic hydrocarbon fluid having a minimum IPB of 218° C. and a maximum DP of 257° C. and is a product of ExxonMobil Chemical Corporation.
[4]Exxsol D80 consists mainly of non-aromatic hydrocarbons with an IBP of 200° C. minimum and a DP of 248° C. max.

TABLE 7

| Sample composition | | Result |
|---|---|---|
| Propargyl bromide | Other components | 100 cm |
| 95 wt % | 5 wt % Toluene | no |
| 97.5 wt % | 2.5 wt % Toluene | yes |
| 95 wt % | 5 wt % Exxsol D80[1] | no |
| 95 wt % | 5 wt % Exxsol D80[1] | no |
| 97.5 wt % | 2.5 wt % Exxsol D80[1] | yes |
| 98 wt % | 2 wt % Exxsol D80[1] | yes |
| 95 wt % | 5 wt % Soygold 1000[2] | yes |
| 92.5 wt % | 7.5 wt % Soygold 1000[2] | no |
| 95 wt % | 5 wt % DF#9[3] | yes |
| 92.5 wt % | 7.5 wt % DF#9[3] | no |
| 95 wt % | 5 wt % Isopar M[4] | no |
| 97.5 wt % | 2.5 wt % Isopar M[4] | yes |
| 95 wt % | 5 wt % Cyclohexane | no |
| 97.5 wt % | 2.5 wt % Cyclohexane | no |
| 95 wt % | 5 wt % n-Heptane | no |
| 97.5 wt % | 2.5 wt % n-Heptane | yes |
| 74.9 wt % | 10 wt % Cyclohexane, 10 wt % Soygold 1000[2], 5 wt % ESO, 0.1 wt % BHT | no |
| 74.9 wt % | 10 wt % Cyclohexane, 10 wt % Exxsol D80[1], 5 wt % ESO, 0.1 wt % BHT | no |
| 74.9 wt % | 10 wt % Cyclohexane, 10 wt % DF#9[3], 5 wt % ESO, 0.1 wt % BHT | no |
| 74.9 wt % | 10 wt % Cyclohexane, 10 wt % toluene, 5 wt % ESO, 0.1 wt % BHT | no |
| 74.9 wt % | 10 wt % Cyclohexane, 10 wt % Isopar E[4], 5 wt % ESO, 0.1 wt % BHT | no |
| 77 wt % | 10 wt % Cyclohexane, 9.5 wt % Isopar E[4], 3 wt % ESO, 0.5 wt % BHT | no |
| 67.5 wt % | 31 wt % Isopar C[5], 1 wt % ESO, 0.5 wt % BHT | no |
| 67.5 wt % | 31 wt % Isopar C[5], 1 wt % ESO, 0.5 wt % BHT (at 50° C.) | no |

TABLE 7-continued

Sample composition

| Propargyl bromide | Other components | Result 100 cm |
|---|---|---|
| 0 wt % | 100 wt % 1,3-dichloropropene | no |
| 0 wt % | 100 wt % Propargyl alcohol | no |

[4]Isopar E is a non-aromatic hydrocarbon fluid having a minimum IBP of 113° C., a 50% recovered temperature in the range of 116–128° C., and a maximum DP of 143° C. and is a product of ExxonMobil Chemical Company.
[5]Isopar C (ExxonMobil Company) is an isoparaffinic hydrocarbon mixture, predominately of $C_8$ isomers, and apparently contains about 80% of isooctane.

Example 6

The adiabatic compression cell and its parts were designed and fabricated by Safety Consulting Engineers, Inc. (Schaumberg, Ill.).

The adiabatic compression test cell consists of a plunger, ~0.3 inches in diameter, which fits into a cylindrical base. An O-ring makes an airtight seal between the plunger and the base. An aluminum rupture disk (0.020 inches thick) and a PTFE Teflon seal disk (0.039 inches thick) are used to seal the sample chamber and provide pressure relief.

Liquid sample (0.030 mL) was loaded into the bottom of the cell. The gas present during the adiabatic compression test was chosen by loading the cell in either the atmosphere or a nitrogen purged glovebox. The plunger was inserted a fixed distance into the base. A drop weight of 5 kg was used for all trials, and the drop height was varied for some samples. The drop weight was allowed to strike the plunger. Results were recorded as "go" or "no". A "go" (reaction) is defined as an impact that produces one or more of the following phenomena: (a) audible report, (b) flame or visible light, (c) definite evidence of smoke (not to be confused with a fume), and (d) definite evidence of discoloration of the sample due to decomposition. Table 8 summarizes the results for the samples tested in air; Table 9 summarizes the results for the samples tested under nitrogen. In both Tables, the "# Go" and "# No" show how many trials of the total for the set had that result. For the sets using several different drop heights, a range is reported. The 50% Go/No Height is a statistically determined value at which half of trials should result in "Go" and the other half in "No".

TABLE 8

| Set | Propargyl bromide | Other components | Total # of trials | # Go | # No | Drop Height | 50% Go/No height | Observations |
|---|---|---|---|---|---|---|---|---|
| 2 | 100 wt % | 0 wt % | 5 | 5 | 0 | 5–10 cm | <5 cm | audible report, smoke, and soot |
| 4 | 80 wt % | 20 wt % Toluene | 4 | 4 | 0 | 5 cm | <5 cm | smoke and soot |
| 5 | 80 wt % | 20 wt % Exxsol D80[1] | 10 | 10 | 0 | 5–96 cm | <5 cm | smoke and soot |
| 6 | 80 wt % | 20 wt % Soygold 1000[2] | 4 | 4 | 0 | 5 cm | <5 cm | smoke and soot |
| 7 | 80 wt % | 20 wt % A150[3] | 7 | 6 | 1 | 5 cm | <5 cm[4] | smoke and soot |
| 8 | 80 wt % | 20 wt % Isopar M[5] | 4 | 4 | 0 | 5 cm | <5 cm | smoke and soot; faint "pop" in three trials |
| 9 | 80 wt % | 20 wt % Cyclohexane | 4 | 4 | 0 | 5 cm | <5 cm | smoke and soot; faint "pop" in two trials |
| 10 | 80 wt % | 13 wt % A150ND[3], 7 wt % epoxidized soybean oil | 5 | 4 | 1 | 5 cm | <5 cm[6] | smoke seen in four trials; soot seen in two of these trials |
| 16 | 74.9 wt % | 10 wt % Exxsol D80[1], 10 wt % cyclohexane, 5 wt % epoxidized soybean oil, 0.1 wt % BHT[7] | 1 | 1 | 0 | 5 cm | <5 cm | faint audible report, smoke, char |
| 22 | 67.5 wt % | 31 wt % Isopar C[8], 1 wt % epoxidized soybean oil, 0.5 wt % BHT[7] | 4 | 4 | 0 | 5 & 96 cm | <5 cm | faint audible report, smoke, char |
| 11 | 64.9 wt % | 20 wt % Exxsol D80[1], 10 wt % cyclohexane, 5 wt % epoxidized soybean oil, 0.1 wt % BHT[7] | 4 | 4 | 0 | 5 cm | <5 cm | smoke and soot; faint "pop" |
| 20 | 50 wt % | 50 wt % Exxsol D80[1] | 1 | 1 | 0 | 5 cm | <5 cm | faint audible report, smoke, char |
| 17 | 0 wt % | 100 wt % Soygold 1000[2] | 4 | 2 | 2 | 5–96 cm | "Go" as low as 10 cm | "Go" trials: white smoke, discoloration of liquid |
| 18 | 0 wt % | 100 wt % Cyclohexane | 2 | 2 | 0 | 5 & 10 cm | "Go" as low as 5 cm | smoke, discoloration of liquid |
| 1 | 0 wt % | Nitromethane (99+%; Aldrich) | 21 | 12 | 9 | 6.5–12.5 cm | 7.7 cm | all "Go" trials: audible report and smoke; five of these burst the rupture disk |

[4]One test out of seven was a "no" from 5.0 cm.
[6]One test out of five was a "no" from 5.0 cm.

TABLE 9

| | Sample composition (N₂ atm.) | | | | | | |
|---|---|---|---|---|---|---|---|
| Set | Propargyl bromide | Other components | Total # of trials | # Go | # No | Drop height | 50% Go/No height | Comments |
| 3 | 100 wt % | 0 wt % | 14 | 2 | 12 | 90.2 & 96 cm | ≧96 cm[1] | all "Go" results: audible report, smoke, and soot |
| 12 | 74.9 wt % | 10 wt % toluene, 10 wt % cyclohexane, 5 wt % epoxidized soybean oil, 0.1 wt % BHT[2] | 10 | 0 | 10 | 96 cm | >96 cm | two trials showed slight discoloration |
| 13 | 74.9 wt % | 10 wt % Soygold 1000[3], 10 wt % cyclohexane, 5 wt % epoxidized soybean oil, 0.1 wt % BHT[2] | 10 | 0 | 10 | 96 cm | >96 cm | — |
| 14 | 74.9 wt % | 10 wt % Exxsol D80[4], 10 wt % cyclohexane, 5 wt % epoxidized soybean oil, 0.1 wt % BHT[2] | 10 | 0 | 10 | 96 cm | >96 cm | — |
| 15 | 74.9 wt % | 10 wt % DF#9[5], 10 wt % cyclohexane, 5 wt % epoxidized soybean oil, 0.1 wt % BHT[2] | 10 | 0 | 10 | 96 cm | >96 cm | — |
| 21 | 67.5 wt % | 31 wt % Isopar C[6], 1 wt % epoxidized soybean oil, 0.5 wt % BHT[2] | 4 | 0 | 4 | 96 cm | >96 cm | Faint audible report, smoke, and soot |

[1]At 96.0 cm, two of eleven experiments resulted in "go". The remaining nine experiments, and an additional two experiments at 90.2 cm, resulted in "no".

Example 7

Tests were performed to determine the initiation sensitivity of propargyl bromide and propargyl bromide formulations to sudden gas compression (adiabatic compression). The instantaneous compression of air in the test cell simulates various conditions. Such conditions include pressure waves from an opening/closing valve or a pump (pump ripple); a water hammer; the presence of air and/or gas bubbles in liquid.

An adiabatic compression cell was used in conjunction with a Bureau of Mines (BOM) drop impact tester. If a reaction occurred with a drop height less than 100 cm, the material was too hazardous to pump. For all trials, the drop weight was 5 kg; sample size was 2 drops (~30~40 mg). Some trials were run under nitrogen (to minimize or exclude oxygen). A "yes" (GO) result indicated that decomposition occurred, while a "no" result (NO GO) indicated that no decomposition occurred. Results for tests under air are summarized in Table 10; Table 11 summarizes results for test conducted under nitrogen.

TABLE 10

| Sample composition | | | | |
|---|---|---|---|---|
| Propargyl bromide | Other components | Atm. | Drop height | Result |
| 100 wt % | 0 wt % | air | 150 cm | yes; smoke, soot |
| | | | 100 cm | yes; smoke, soot; rupture disc burst |
| 80 wt % | 20 wt % toluene | air | 150 cm | yes; soot-like residue |
| | | | 125 cm | yes; soot-like residue |
| | | | 100 cm | yes; smoke and soot |
| | | | 100 cm | yes; soot-like residue |
| | | | 75 cm | yes; soot-like residue |
| | | | 60 cm | yes; soot-like residue |
| | | | 40 cm | yes; soot-like residue |
| | | | 30 cm | yes; soot-like residue |
| | | | 20 cm | yes; soot-like residue |
| | | | 15 cm | yes; soot-like residue |
| | | | 10 cm | yes; soot-like residue |

TABLE 10-continued

| Sample composition | | | | |
|---|---|---|---|---|
| Propargyl bromide | Other components | Atm. | Drop height | Result |
| 70 wt % | 23 wt % Aromatic 150[1], 7 wt % epoxidized soybean oil | air | 100 cm | yes; soot-like residue |
| | | | 60 cm | yes; soot-like residue |
| | | | 40 cm | yes; soot-like residue |
| | | | 30 cm | yes; soot-like residue |
| | | | 20 cm | yes; soot-like residue |
| | | | 10 cm | no |
| 0 wt % | nitromethane* | air | 75 cm | yes |
| | | | 60 cm | yes |
| | | | 30 cm | yes |
| | | | 20 cm | yes |
| | | | 15 cm | no |
| | | | 15 cm | no |
| | | | 15 cm | yes |

[1]Aromatic 150 is more than 99% pure naphthalene-depleted C₇₋₉ aromatic hydrocarbons (CAS 70693-06-0).
*For each "yes" result, the rupture disc burst and/or the piston forcefully pushed out the compression cell.

TABLE 11

| Sample composition | | | | |
|---|---|---|---|---|
| Propargyl bromide | Other components | Atmosphere | Drop height | Result |
| 100 wt % | 0 wt % | partial reduction of O₂ with N₂ | 100 cm | yes |
| | | | 80 cm | yes |
| | | | 60 cm | yes |
| | | | 40 cm | yes |
| | | | 35 cm | yes |
| | | | 25 cm | yes |
| | | | 20 cm | yes |
| | | | 15 cm | no |
| | | | 10 cm | yes |
| | | | 10 cm | yes |
| 100 wt % | 0 wt % | N₂ | 30 cm | no |
| | | | 50 cm | no |
| | | | 75 cm | no |
| | | | 100 cm | no |
| | | | 100 cm | no |
| | | | 100 cm | no |

TABLE 11-continued

| Sample composition | | Atmosphere | Drop height | Result |
|---|---|---|---|---|
| Propargyl bromide | Other components | | | |
| | | | 150 cm | no; slight discoloration of liquid sample |
| | | | 150 cm | no; slight discoloration of liquid sample |
| | | | 150 cm | no; slight discoloration of liquid sample |
| 80 wt % | 20 wt % toluene | N$_2$ | 125 cm | no |
| | | | 100 cm | no |
| | | | 100 cm | no |
| | | | 100 cm | no |
| | | | 125 cm | no |
| | | | 150 cm | no; slight discoloration of liquid sample |
| | | | 150 cm | no; slight discoloration of liquid sample |
| | | | 150 cm | no; slight discoloration of liquid sample |
| | | | 150 cm | no; slight discoloration of liquid sample |

Example 8

Differential scanning calorimetry (DSC) tests were performed on propargyl bromide formulations to determine the combustion (exothermic peak) temperature and melting (endothermic) temperature of each formulation. A Differential Scanning Calorimeter (TA Instruments, model 2910) was utilized. The material was placed into the sample holder of the calorimeter, and heated at a rate of 10° C. per minute. For this heating rate, the temperature at which maximum heat output rate occurred was defined as the peak exothermic temperature of the sample. Both the onset temperature and maximum heat output rate temperature were recorded. If the onset exotherm is less than 100° C., the material is regarded as being too hazardous to ship. The onset and exothermic peak temperature results for the propargyl bromide formulations tested are shown in Table 12.

TABLE 12

| Sample composition | | Onset Temperature | Peak Exothermic Temperature |
|---|---|---|---|
| Propargyl bromide | Other components | | |
| 100 wt % | 0 wt % | 233° C. | 299° C. |
| 80 wt % | 16 wt % Aromatic 150, 4 wt % epoxidized soybean oil | 226° C. | 355° C. |
| 80 wt % | 13 wt % Aromatic 150, 7 wt % epoxidized soybean oil | 226° C. | 310° C. |
| 70 wt % | 26 wt % Aromatic 150, 4 wt % epoxidized soybean oil | 226° C. | 306° C. |
| 70 wt % | 23 wt % Aromatic 150, 7 wt % epoxidized soybean oil | 225° C. | 306° C. |
| 100 wt % | 0 wt % | 173° C. | 245° C. |

Example 9

Propargyl bromide and formulations thereof underwent testing to determine their sensitivity to intensive heat under confinement, sometimes called a Koenen test. An aperture disc with an adjustable orifice diameter was used; the diameter was set to 1.0 mm for all runs. The test results are assessed on the basis of the tube fragmentation type and limiting diameter of the orifice allowing the by-product to escape under test conditions when subjected to intense heat. Under United Nations standards, the result is considered positive if the substance shows violent effect on heating under confinement when the limiting diameter of the orifice disk is 2.0 mm or larger. The result is considered negative if the substance shows no violent effect on heating under confinement when the limiting diameter of the orifice disk is less than 2.0 mm. The results are summarized in Table 13.

TABLE 13

| Sample composition | | Sample weight | Time-to-Reaction | Tube Condition | Overall Result Explosion |
|---|---|---|---|---|---|
| Propargyl bromide | Other components | | | | |
| 80 wt % | 13 wt % Aromatic 150, 7 wt % epoxidized soybean oil | 37.6 g | 10 sec smoke 60 sec smoke + fire 75 sec no smoke | unchanged, no damage | no |
| | | 37.7 g | 12 sec smoke 70 sec smoke + fire 80 sec no smoke | unchanged, no damage | no |
| | | 40.9 g | 14 sec smoke 80 sec no smoke | unchanged, no damage | no |
| | | 40.5 g | 12 sec smoke 90 sec no smoke | unchanged, no damage | no |
| | | 40.8 g | 13 sec smoke 85 sec no smoke | unchanged, no damage | no |

Example 10

Propargyl bromide formulations were tested to determine their sensitivity to detonative shock while confined in a heavy steel tube. Each formulation was placed in an uncapped steel cylinder, 4 inches long, having a 1.5 inch outer diameter and a 0.5-inch inner diameter. The witness plate, 3 inches×3 inches×0.75 inches thick, is positioned at the bottom end of the tube while a pentolite booster is placed at the top end of the tube. A blasting cap is utilized to initiate the booster. The reaction is considered positive if a hole is punched through the witness plate and/or if the steel cylinder (pipe container) is fragmented entirely. The results for the propargyl bromide formulations tested are summarized in Table 14.

TABLE 14

| Sample composition | | Observations | | |
| --- | --- | --- | --- | --- |
| Propargyl bromide | Other components | Witness Plate | Steel Tube/Pipe | Results |
| 100 wt % | 0 wt % | No damage and/or dent on plate | not found | no |
| 100 wt % | 0 wt % | No damage and/or dent on plate | split half open | no |
| 80 wt % | 16 wt % Aromatic 150, 4 wt % epoxidized soybean oil | No damage and/or dent on plate | split half open | no |
| 80 wt % | 13 wt % Aromatic 150, 7 wt % epoxidized soybean oil | No damage and/or dent on plate | no visual damage | no |
| 70 wt % | 26 wt % Aromatic 150, 4 wt % epoxidized soybean oil | No damage and/or dent on plate | no visual damage | no |
| 70 wt % | 23 wt % Aromatic 150, 7 wt % epoxidized soybean oil | No damage and/or dent on plate | no visual damage | no |
| 0 wt % | 100 wt % H$_2$O | No damage and/or dent on plate | split, but still held together | no |

It is to be understood that the ingredients referred to by chemical name or formula anywhere in the specification or claims hereof, whether referred to in the singular or plural, are identified as they exist prior to coming into contact with another substance referred to by chemical name or chemical type (e.g., another reactant, a solvent, a diluent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and other materials are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance or ingredient as it existed at the time just before it was first contacted, blended or mixed with one or more other substances or ingredients in accordance with the present disclosure. The fact that the substance or ingredient may have lost its original identity through a chemical reaction or transformation or complex formation or assumption of some other chemical form during the course of such contacting, blending or mixing operations, is thus wholly immaterial for an accurate understanding and appreciation of this disclosure and the claims thereof. Nor does reference to an ingredient by chemical name or formula exclude the possibility that during the desired reaction itself an ingredient becomes transformed to one or more transitory intermediates that actually enter into or otherwise participate in the reaction. In short, no representation is made or is to be inferred that the named ingredients must participate in the reaction while in their original chemical composition, structure or form.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of preparing propargyl bromide, which process comprises reacting in a reaction zone phosphorus tribromide and propargyl alcohol in an inert liquid azeotropic solvent that forms an azeotrope with propargyl bromide, to form a reaction mass containing propargyl bromide and said azeotropic solvent, and separating a mixture consisting essentially of propargyl bromide and said azeotropic solvent from the reaction mass, whereby a stabilizing amount of said azeotropic solvent is present with the propargyl bromide both in the liquid state and in the vapor phase (i) during the time the propargyl bromide is being formed and (ii) during and after the time propargyl bromide is being separated from the reaction mass.

2. A process of claim 1 wherein said liquid solvent consists essentially of a paraffinic and/or cycloparaffinic hydrocarbon solvent.

3. A process of claim 1 wherein said liquid solvent consists essentially of a mixture of $C_8$ paraffinic hydrocarbons.

4. A process of claim 1 wherein said mixture consisting essentially of propargyl bromide and said azeotropic solvent is separated from the reaction mass by distillation.

5. A process of claim 4 wherein said liquid solvent consists essentially of a paraffinic and/or cycloparaffinic hydrocarbon solvent.

6. A process of claim 4 wherein said liquid solvent consists essentially of a mixture of $C_8$ paraffinic hydrocarbons.

7. A process of preparing propargyl bromide, which process comprises bringing together in a reaction zone, components comprising phosphorus tribromide, propargyl alcohol, and a stabilizing agent, in the presence of an amine catalyst, wherein a stabilizing amount of said agent is present (i) during the time the phosphorus tribromide and the propargyl alcohol are being brought together, (ii) during the time propargyl bromide is being formed, and (iii) during and after the time propargyl bromide is being separated from by-products formed in the process, and wherein said stabilizing agent is comprised of:

A) one or a mixture of $C_{7-8}$ saturated hydrocarbons optionally along with up to about 50 wt %, based on the total weight of A), of (1) one or more $C_6$ saturated hydrocarbons or (2) one or more $C_9$ saturated hydrocarbons, or (3) both of (1) and (2); or B) a mixture of about 10 to about 90 wt % of one or more $C_6$ saturated hydrocarbons and about 90 to about 10 wt % of one or more $C_9$ saturated hydrocarbons.

8. A process as in claim 7 wherein at least 95 wt % of said agent is A) or B).

9. A process as in claim 8 wherein at least 97 wt % of said agent is A).

10. A process as in claim 8 wherein at least 97 wt % of said agent is B).

11. A process as in claim 7 wherein up to about 5 wt % of said agent is one or more liquid hydrocarbons other than any hydrocarbon as defined in A) or in B).

12. A process as in claim 7 wherein up to about 10 wt % of said agent is toluene, one more xylene isomers, one or more non-cyclic ethers, tetrahydrofuran, dioxane, beta-ionone, ethanol, or a mixture of any two or more of the foregoing.

13. A process as in claim 12 wherein up to about 5 wt % of said agent is toluene.

14. A process as in claim 7 wherein said amine catalyst is a trihydrocarbylamine.

15. A process as in claim 14 wherein said trihydrocarbylamine is at least one amine selected from the group consisting of triarylamines and trialkylamines.

16. A process as in any of claims 7, 8, 9, or 12 wherein propargyl bromide together with at least 10 wt % of A) or B) are separated from said by-products by distillation, and remain together with propargyl bromide in the condensed distillate, said wt % being based on the total weight of propargyl bromide and said one or more saturated hydrocarbons in the condensed distillate.

17. A process as in claim 16 further comprising introducing at least one antioxidant or at least one acid scavenger, or both, into said condensed distillate.

18. A process as in claim 17 wherein said at least one antioxidant is at least one sterically hindered phenolic antioxidant and said at least one acid scavenger is at least one epoxide or epoxidized olefinically unsaturated oil.

19. A process of preparing propargyl bromide, which process comprises cofeeding to a reaction zone, components comprising phosphorus tribromide, propargyl alcohol, a stabilizing agent, and an amine catalyst, wherein phosphorus tribromide and propargyl alcohol are fed separately from each other, and wherein a stabilizing amount of said agent is present (i) during the time the phosphorus tribromide and the propargyl alcohol are being brought together, (ii) during the time propargyl bromide is being formed, and (iii) during and after the time propargyl bromide is being separated from by-products formed in the process.

20. A process as in claim 19 wherein said stabilizing agent is comprised of at least about 95 wt % based on the total weight of the agent of:
A) one or a mixture of $C_{7-8}$ saturated hydrocarbons optionally along with up to about 50 wt %, based on the total weight of A), of (1) one or more $C_6$ saturated hydrocarbons or (2) one or more $C_9$ saturated hydrocarbons, or (3) both of (1) and (2); or
B) a mixture of about 10 to about 90 wt % of one or more $C_6$ saturated hydrocarbons and about 90 to about 10 wt % of one or more $C_9$ saturated hydrocarbons; or
C) toluene, one more xylene isomers, one or more non-cyclic ethers, tetrahydrofuran, dioxane, beta-ionone, ethanol, or a mixture of any two or more of these components of C).

21. A process as in claim 20 wherein at least 95 wt % of said agent is A) or B).

22. A process as in claim 21 wherein at least 97 wt % of said agent is A).

23. A process as in claim 21 wherein at least 97 wt % of said agent is B).

24. A process as in claim 20 wherein up to about 5 wt % of said agent is one or more liquid hydrocarbons other than any hydrocarbon as defined in A) or in B).

25. A process as in claim 21 wherein up to about 5 wt % of said agent is toluene, one more xylene isomers, one or more non-cyclic ethers, tetrahydrofuran, dioxane, beta-ionone, ethanol, or a mixture of any two or more of the foregoing.

26. A process as in claim 25 wherein up to about 5 wt % of said agent is toluene.

27. A process as in claim 19 wherein said amine catalyst is a trihydrocarbylamine.

28. A process as in claim 27 wherein said trihydrocarbylamine is at least one amine selected from the group considering of triarylamines and trialkylamines.

29. A process as in any of claims 19, 20, or 22 wherein propargyl bromide together with at least 10 wt % of A) or B) are separated from said by-products by distillation, and remain together with propargyl bromide in the condensed distillate, said wt % being based on the total weight of propargyl bromide and said one or more saturated hydrocarbons in the condensed distillate.

30. A process as in claim 29 further comprising introducing at least one antioxidant or at least one acid scavenger, or both, into said condensed distillate.

31. A process as in claim 30 wherein said at least one antioxidant is at least one sterically hindered phenolic antioxidant and said at least one acid scavenger is at least one epoxide or epoxidized olefinically unsaturated oil.

* * * * *